(12) United States Patent
Virág

(10) Patent No.: US 6,249,344 B1
(45) Date of Patent: Jun. 19, 2001

(54) METHOD AND APPARATUS FOR SEDIMENTATION AND OPTICAL EXAMINATION OF PARTICLES SUSPENDED IN A FLUID, FURTHER A CUVETTE FOR ACCOMPLISHING SAID METHOD

(75) Inventor: Tibor Virág, Budapest (HU)

(73) Assignee: Roche Diagnostics, GmbH, Mannheim (DE)

( * ) Notice: Subject to any disclaimer, the term of this patent is extended or adjusted under 35 U.S.C. 154(b) by 0 days.

(21) Appl. No.: 09/068,460

(22) PCT Filed: Nov. 15, 1996

(86) PCT No.: PCT/HU96/00068

§ 371 Date: Jun. 17, 1998

§ 102(e) Date: Jun. 17, 1998

(87) PCT Pub. No.: WO97/18458

PCT Pub. Date: May 22, 1997

(30) Foreign Application Priority Data

Nov. 16, 1995 (HU) .................... 9503278

(51) Int. Cl.⁷ ............................ G01N 21/01
(52) U.S. Cl. ........................ 356/244; 356/246
(58) Field of Search ........................ 356/244, 246, 356/318, 319, 436; 366/219, 240; 435/288.3, 305.1

(56) References Cited

U.S. PATENT DOCUMENTS

| 3,141,547 | * | 7/1964 | Newby ................. 356/318 |
| 3,873,021 | * | 3/1975 | Paulsen . |
| 4,452,902 | * | 6/1984 | Suovaniemi et al. . |
| 4,595,563 | * | 6/1986 | Degrave . |
| 4,609,991 | * | 9/1986 | Minton et al. ............ 356/318 |
| 4,895,453 | * | 1/1990 | Devlin et al. ............ 366/219 |

FOREIGN PATENT DOCUMENTS

0628824A1 * 12/1994 (EP) ........................ 35/4

* cited by examiner

Primary Examiner—Frank G. Font
Assistant Examiner—Tu T. Nguyen
(74) Attorney, Agent, or Firm—Nikaido Marmelstein Murray & Oram, LLP.

(57) ABSTRACT

An apparatus for sedimentation comprising: a cuvette holder configured to receive a cuvette containing a sample liquid containing particle; and a centrifuge having a horizontal shaft which is coupled to the cuvette holder such that the cuvette holder can assume a plurality of rotational positions about the horizontal shaft and configured such that the cuvette holder is substantially horizontal when the cuvette holder is in a lowermost position relative to the horizontal shaft.

29 Claims, 3 Drawing Sheets

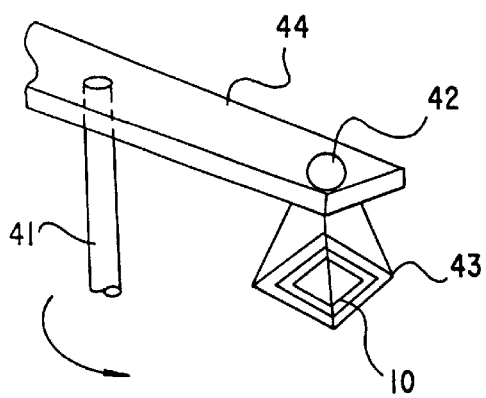
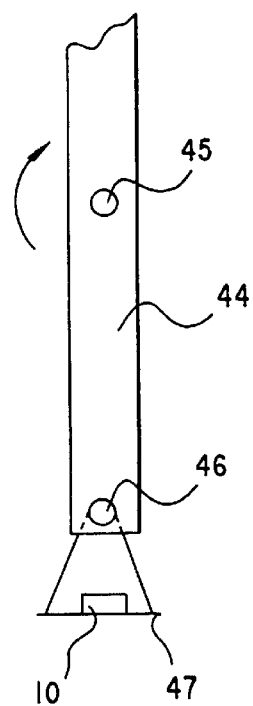
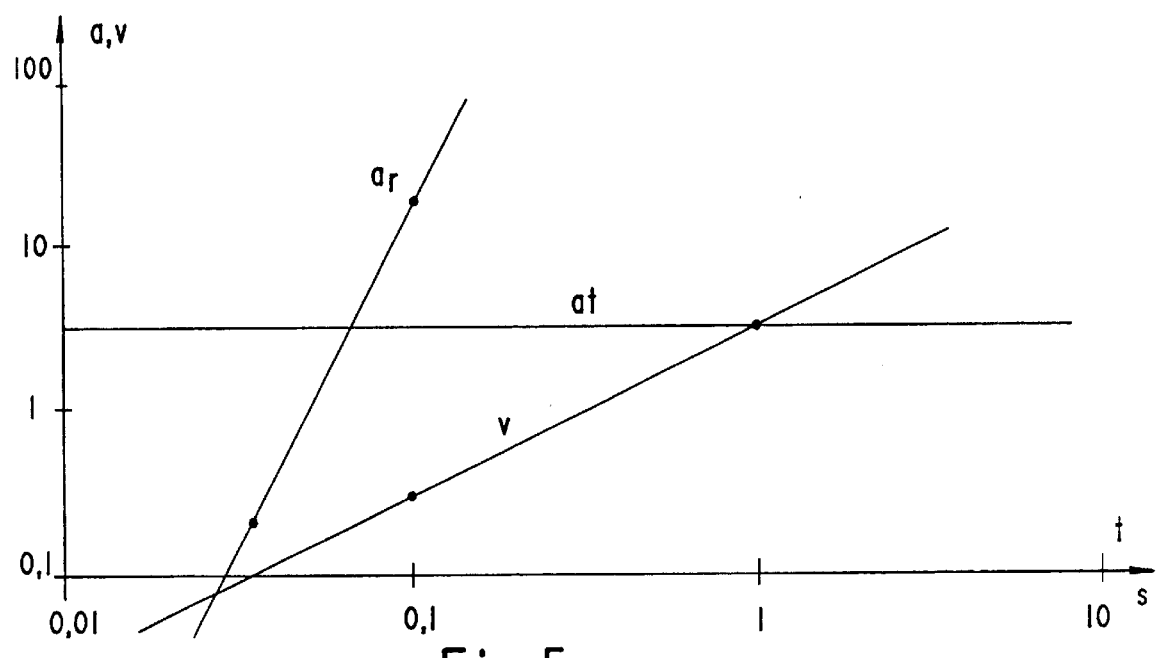

METHOD AND APPARATUS FOR SEDIMENTATION AND OPTICAL EXAMINATION OF PARTICLES SUSPENDED IN A FLUID, FURTHER A CUVETTE FOR ACCOMPLISHING SAID METHOD

FIELD OF THE INVENTION

The present invention relates to a method and an apparatus for sedimentation and optical examination of particles suspended in a fluid, further a cuvette to accomplish said method.

BACKGROUND OF THE INVENTION

In laboratory practice the necessity of optical., microscopic examination of particles suspended in a fluid (emulsion or suspension) often arises to classify the particles according to their shape and determine concentrations of various fractions. In medical practice, determination of blood cell counts or analysis of urine sediments may constitute such tasks. Several similar examinations are carried out in other fields of industry, e.g. in food processing or pharmaceutical industry.

Such examinations are conventionally performed by filling the sample into a test tube, sedimentation it by centrifuging for a required period, removing the supernatant, homogenizing and staining the sediment if required, and transferring a drop of it to a microscope slide, covering it with a coverslip and evaluating the observed image with human eye through a microscope, and repeating this evaluation on a required number of imaging areas.

The above traditional method is extraordinarily inaccurate, time-consuming and can hardly be automated. Numerous methods have been developed to simplify the conventional method.

According to a known method suitable for investigating particles suspended in a fluid, the sample of considerable volume is passed through a flow-cell and the particles flowing in the sample are optically observed and analysed. Such methods are described in Patent Specifications of No. U.S. Pat. Nos. 4,393,466 and 5,123,055.

Deficiency of the methods known so far is that the moving particles can be observed optically for a very short time only, therefore, owing to the limited time available for classifying each particle, practically there is no way to perform morphological testing.

DISCLOSURE OF THE INVENTION

The object of the invention is to provide an improved method lending itself to easy automation, beside being quick and relatively accurate.

Another object of the invention is to provide an apparatus suitable for preparing particles suspended in a fluid for optical examination.

A further aim of the invention is to develop a cuvette permitting quick preparation of particles suspended in a fluid for optical examination and to perform said optical examination by means of the said cuvette.

According to one aspect of the invention a method is provided for sedimentation and optically examining particles suspended in a fluid, in the course of which the sample to be tested is settled, and the sediment is examined optically. This method comprises the following steps: placing the sample stained as required into a cuvette provided with a planar baseplate and sedimentation it therein, and after sedimentation optically examining the sample from below, with cuvette held in horizontal position.

According to a preferred embodiment of the invented method the sedimentation of sample is carried out by centrifuging. Further, it is preferred that the ratio between the component of acceleration perpendicular to baseplate and the component parallel to the latter and acting on said cuvette be maintained at a value higher than 10.

According to another aspect of the invention a device is provided for implementing the method. The invented apparatus comprises a conveyor and a cuvette dosing device arranged along said conveyor, further a moving mechanism forwarding the cuvettes along the conveyor and a sample feeder, wherein the cuvettes are provided with a planar baseplate. Along the conveyor a centrifuge is arranged which is followed by an optical unit consisting of a microscope objective and a horizontally positioned object platform having an opening therein. Said microscope objective placed under said object platform.

In a preferred embodiment of the device said centrifuge is provided with a self-aligning cuvette holder mounted to an arm. The centrifuge can be fitted with a vertical shaft to which the cuvette holder is coupled through a pivotal joint permitting rotation in two degrees of freedom.

In a further preferred version the centrifuge is fitted with a horizontal shaft. Said cuvette holder is mounted onto the shaft through either a fixed or a pivoting joint permitting rotation around an axis parallel with the horizontal shaft, if said joint is of a fixed type it is to fix said cuvette holder in a fixed position with respect to said shaft. This fixed position is both parallel with the axis of the shaft and horizontal while the shaft is in its end position after finishing centrifugation. This is the lowermost position of the cuvette in the centrifuge and it is oriented horizontally for preventing tangential displacement of the sediment. The centrifuge should start preferably from the same angular position to keep the cuvette horizontal before centrifugation.

Said object platform and microscope objective of the optical unit are coupled to each other preferably by a sealing permitting axial displacement, said sealing confining a vacuum chamber between said microscope objective and said object platform. A vacuum pump is connected through a vacuum connecting pipe to said vacuum chamber. The suction provided by said vacuum pump presses the cuvette against said platform and thereby the distance of the cuvette baseplate to the microscope objective can be kept constant.

According to a further aspect of the invention a cuvette is provided for implementing of the above method and for being used in conjunction with the apparatus described above. Said cuvette is provided with a planar baseplate and a coverplate is attached to said baseplate, through a frame of uniform thickness. Said cuvette is further provided with an opening for filling the sample into the interior of said cuvette. Said baseplate of said cuvette is resilient to a measure enabling its resilient deformation to fit closely to the periphery of said opening provided in the object platform of said optical unit.

In a preferred embodiment of said cuvette said opening for filling in the sample is leading through the frame and is in fluid communication with the space confined by baseplate and coverplate. Said opening is fitted with a plug for shutting off the opening.

BRIEF DESCRIPTION OF THE DRAWINGS

The invention, its further features and advantages are discussed by referring to the attached drawing. In the drawings.

DETAILED DESCRIPTION OF PREFERRED EMBODIMENTS

According to the method complying with the invention, the sample—stained as required—is poured into a flat cuvette, the cuvette is centrifuged and, in the course of centrifuging, the acceleration perpendicular to the bottom plane is selected at least ten times higher than that parallel to said plane. After centrifuging for a period required the sample in the cuvette is optically examined from below with the cuvette in horizontal position.

Figure 1:
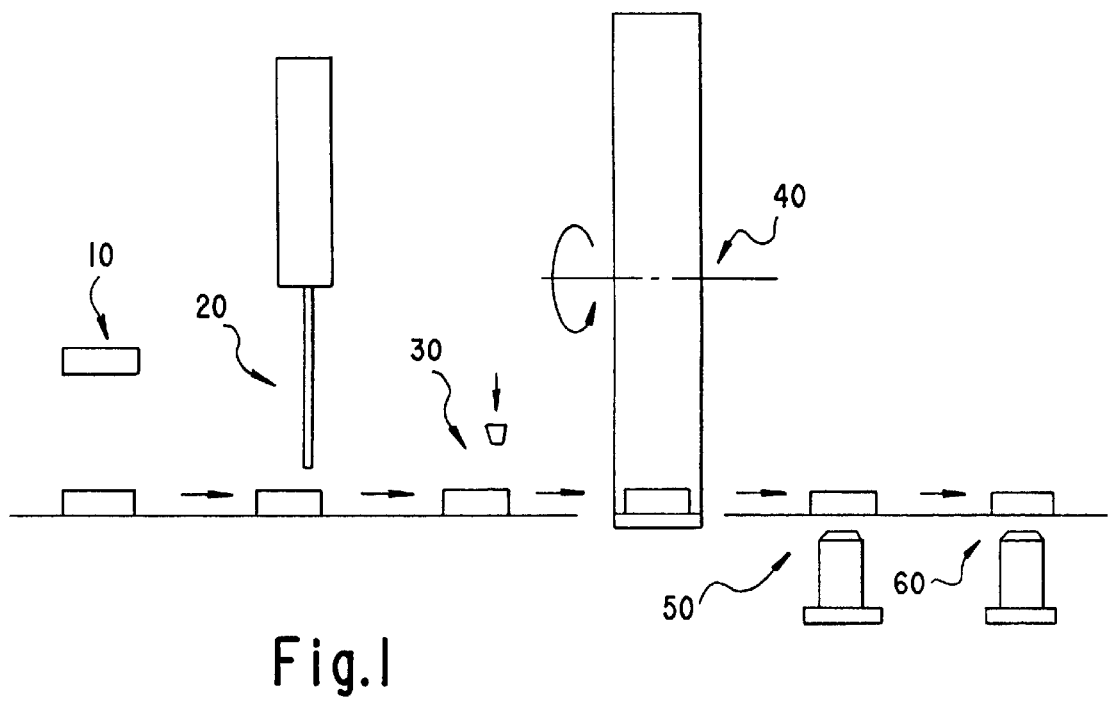
FIG. 1. is a schematic diagram of the device for performing the method complying with the invention, FIG. 2. is the front view of the cuvette for use with the method according to the invention, FIG. 3. is a variant of the centrifuge suitable for centrifuging the cuvette shown in FIG. 2 and having a vertical-axis, FIG. 4. is another variant of the centrifuge suitable for centrifuging the cuvette shown in FIG. 2, having horizontal-axis FIG. 5. is a logarithmic time diagram of the acceleration and deceleration of the sample used with the method complying with the invention, FIG. 6. is a schematic cross-sectional view of the microscopic optical examination, FIG. 7. is a schematic cross-sectional view showing the use of a microscanner for the optical examination of a sample prepared by the invented method.

In FIG. 1. the apparatus for implementing the invented method contains cuvette feeder 16, shown only schematically, serving for placing flat-shape cuvettes, 10 described later in some detail, onto a conveyor belt. By the conveyor belt the cuvettes 10 are transferred to sample doser 20, (shown only diagrammatically), that is suitable for performing also the staining of the samples, if required. From here the filled-up cuvettes 10 get into plugging unit 30, shutting off the cuvettes 10, as required. After that, cuvettes 10 are transferred into the centrifuge arranged along the belt conveyor 17, by which the centrifuging is carried out in a way described further below.

From centrifuge 45 the horizontally positioned cuvettes 10 get into the microscopic optical unit 10 that can be coupled through an image detecting unit (e.g. a video-camera) to a processing unit by which the optical examination is then performed in a known way. Along the conveyor belt, an optical unit 60 suitable for performing further optical examiner e.g. a unit containing a microscanner, can be accommodated, by which further optical examinations can be carried out, if required. In some cases either the microscopic unit 50 or the microscanner unit 60 may be omitted.

Figure 2:
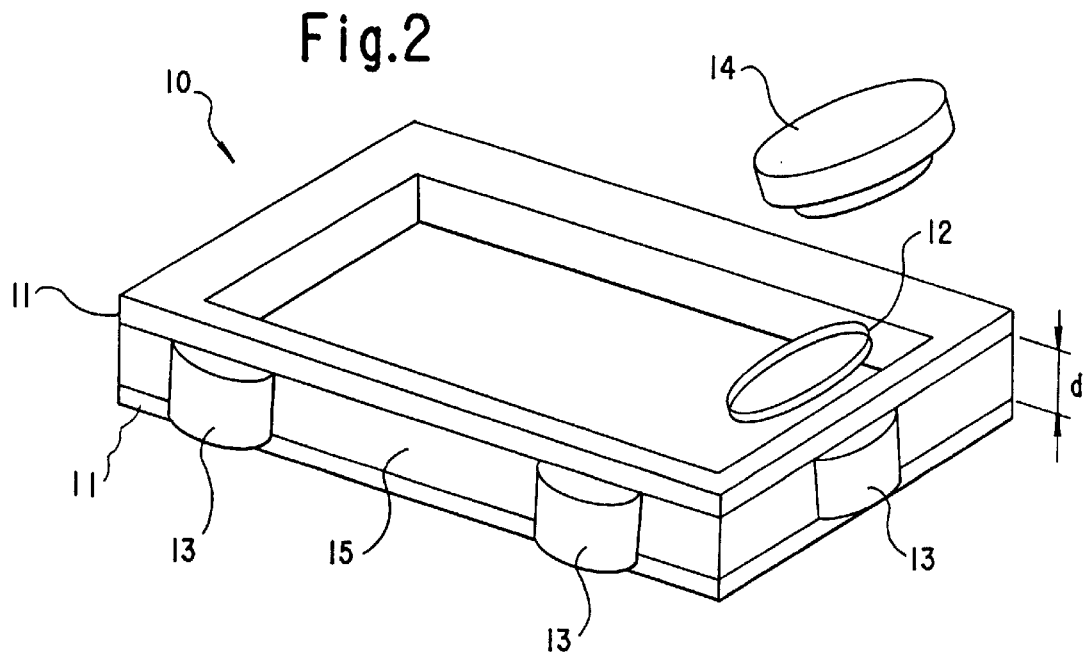

For accomplishing the method complying with the invention an essentially flat-shaped cuvette, i.e. one of small vertical height is required. Such a cuvette is shown in FIG. 2. This cuvette has a baseplate 12 and a coverplate 11, between which the frame 15 determining the height d of the cuvette is located. An opening is provided in coverplate 11 through which the sample to be examined is filed in. Opening may be shut-off with a plug 14, when necessary.

The relatively low height d of cuvette shown in FIG. 2. permits considerable reduction of the sedimentation or centrifuging time. This limited height compared to the conventional 60 to 100 mm long sedimentation paths means a sedimentation path length of 0.2 to 2 mm only. After sedimentation, separation of the settled layer from the so-called supernatant (upper separated layer) would be very difficult, but no such separation is required in the case of the present invention. Instead of that, cuvette 10 has to be moved carefully after centrifuging to prevent relative displacement of the layers. Observing this cautionary measure, the bottom sediment can be examined from below. For this reason the baseplate 12 of cuvette 10 is made of optical-grade glass or plastic having good transparency and constant thickness. Further, it is expedient to select a slightly resilient or flexible material for the baseplate 12 (reason for this will be given further below). For this purpose the material of covering plates, having a thickness of 0.17 mm as commonly used in microscopic examinations will be suitable. Of course, the thickness may be of some other value, e.g. fall in the range of 0.05 to 0.3 mm.

Opening may be connected also to a sidewise passage provided in frame 15 and may be fitted also with a self-closing cover. Locating noses 13 formed on frame 15 facilitate proper lateral positioning and abutment of cuvette 10. However, the provision of these additions are not absolutely necessary.

In the course of implementing the method of complying with the invention, due to the short path length of sedimentation and applying identical acceleration as with conventional centrifuging, the duration of centrifuging is about one hundredth of that required with the conventional method.

This may be advantageous also because the risk of damage of fragile particles present in a tested sample (e.g. cylinders in the urine) is lower than with conventional methods. However, the performance of centrifuging requires special carefulness. After filling in the sample, during the entire period of handling and evaluation, care must be taken to ensure that the forces and accelerations acting on the fluid of the sample and on the suspended or already settled particles, respectively, are perpendicular or at least close to perpendicular to baseplate 12. The possibility of satisfying this requirement is provided by the apparatus complying with the invention, comprising a special centrifuge, a microscope and a conveyor belt forwarding the cuvettes 10.

Of course, centrifuging is only necessary if the shorter spontaneous sedimentation time due to the shorter path length of sedimentation is not sufficient, or if for some other reason it is worth while to make use of the advantages resulting from the shorter path length of sedimentation and from the shorter centrifuging time.

In the course of implementing the method complying with the invention, including also the act of centrifuging, care should be taken to prevent the transient processes taking place at starting and stopping of centrifuge 40 from influencing considerably the movement of the sediment in the case of the very short operation times attributable to the short sedimentation path length. The use of sample holders radially swinging out around a single axis is unsuitable to satisfy these requirements, since during accelerations and decelerations under the effect of considerable tangential forces arising in the sample the sample holder fails to deflect. The arrangement shown in FIG. 3 may be employed instead, where cuvette holder 43 supporting the cuvette 10 is coupled to the arm 44 attached to the upright or vertical shaft 41 through hinge 42 of two degrees for freedom. As regards the design of hinge 42, it may be a ball-and-socked joint or a so-called universal joint having a centre cross. In this case, on starting the centrifuge 45, the cuvette holder 43 can swing both in radial and tangential direction, around hinge 42 like a pendulum, whereby it can be achieved that the accelerations acting on cuvette 10 be perpendicular to the baseplate 12 of cuvette 10. The swings of cuvette holder 43 must not be attenuated by means of damping elements, since these would cause tangential accelerations i.e. having a direction parallel with the baseplate, that may considerably influence the sedimentation process or could cause stirring-up or displacement of the already settled layer. Obviously, the disturbing oscillations of cuvette holder 43 have to be avoided by controlling the acceleration and deceleration of the motor driving the centrifuge.

FIG. 4. illustrates another variant of centrifuge 40, containing an arm 44 mounted on a horizontal shaft 45, and a cuvette holder 47 coupled to said single shaft through joint 46. It is easy to see that, in this case, the cuvette holder 47 is capable of rotating in the plane of rotation, so that it is sufficient to employ a hinge or joint 46 of one degree of freedom. In that case, the insertion of cuvette 10 into the cuvette holder 47 is simpler, and the control of acceleration and deceleration of the driving motor is also simpler. Using a fixed joint instead of said rotating one the centrifuge will not contain any oscillating part, so that transients of the motor and other rotating components coupled thereto have to be considered only. In this case a fixed sample holder is mounted onto the shaft 45 of the centrifuge 40. Said sample holder is oriented to hold the cuvette horizontally in its lowermost position To avoid displacement of the sediment and to keep the cuvette 10 horizontal after finishing centrifugation the shaft 45 has to stop in the same angular position. The centrifuge 40 can be started from the same angular position, thereby spontaneous sedimentation before centrifugation will be oriented vertically to the main plain of said cuvette.

Control of acceleration of centrifuge 40 can be accomplished e.g. according to the diagram of FIG. 5. For the sake of wide range representation, the acceleration, the time and peripheral speed are all shown on a logarithmic scale. Deceleration can also be presented in a similar diagram. In the case illustrated in the figure the radius of centrifuging is 50 mm, the tangential acceleration $a_t$ is 3 m/s$^2$, and the values of the corresponding radial acceleration $a_r$ and peripheral speed v are also given in the diagram in units of m/s and m/s$^2$ units, respectively. It can be seen that in the case of uniform acceleration of such value, a tangential acceleration exceeding the magnitude of radial acceleration will act and will thus be on the sample through a period about 0.05 s only, and the length of this period of time will thus be negligible compared to the full duration of centrifuging. This is particularly true in the case of media of tixotropic character (biological samples are typically such), where no sedimentation at all occurs at low accelerations. In the course of acceleration, the peripheral speed increases linearly in the function of time, while radial acceleration is proportional with the square of time, i.e. compared to radial acceleration the tangential one becomes increasingly negligible already as soon as after 0.2 s.

The effect of tangential acceleration disturbing the sedimentation process can be reduced further by the use of a centrifuge provided with a horizontal or lying shaft 45 and by attaching cuvette 10 not in its lowest, but in its sidewise position with respect to the cuvette holder 47 fitted to arm 44 of centrifuge 40, making the cuvette start downwards from that position.

In typical case the duration of centrifuging is 3 s, during which the centrifuge accelerates from standstill to e.g. 1800 r.p.m., then without running at uniform speed immediately starts decelerating and comes to standstill. During this full period it accomplishes altogether 42 revolutions. It is easy to see that in the very short initial period of centrifuging the condition of keeping the tangential acceleration below one tenth of radial acceleration remains unsatisfied. This short period of time, however, is not sufficient to have a sensible effect on the sedimentation process. If also the gravitational acceleration is considered, this requirement can easily be fulfilled.

Should centrifuge 40 not be fitted with an oscillating cuvette holder, then before starting the centrifuge is brought by quarter of a full revolution in the direction opposite to the subsequent sense of rotation, so as to produce thereby a "run-up" start of the motor. So, at starting, the cuvette assumes vertical position, but in the vertical direction the sedimentation path is considerably longer. So, keeping the cuvette in vertical position for a short time, practically the sedimentation will not be influenced, not even despite the direction of gravitational acceleration being also tangential through this period. Notwithstanding, the duration of this vertical position should be kept as short as possible. After start-up, if a centrifuge fitted with a horizontal or vertical shaft 45 is employed, the magnitude of the applied peripheral acceleration shall be such as to produce a radial acceleration reaching or, at least, approaching the level of gravitational acceleration. When starting is made from the lowest point, the value of peripheral acceleration will be around 3.1 m/s$^2$. A lower acceleration will be required if the centrifuge is started from its angularly displaced in reverse direction. In the following, the peripheral acceleration can be increased proportionally with the square of speed, and the admissible acceleration is limited only by the mechanical parameters of the apparatus. Deceleration has to be performed even more carefully than acceleration, in order to prevent stirring-up and displacement of the already settled layer. At the and of the period of deceleration it shall be tried to bring the arm 44 of centrifuge 40 to standstill, when cuvette 40 just gets in its lower horizontal position.

Figure 6:
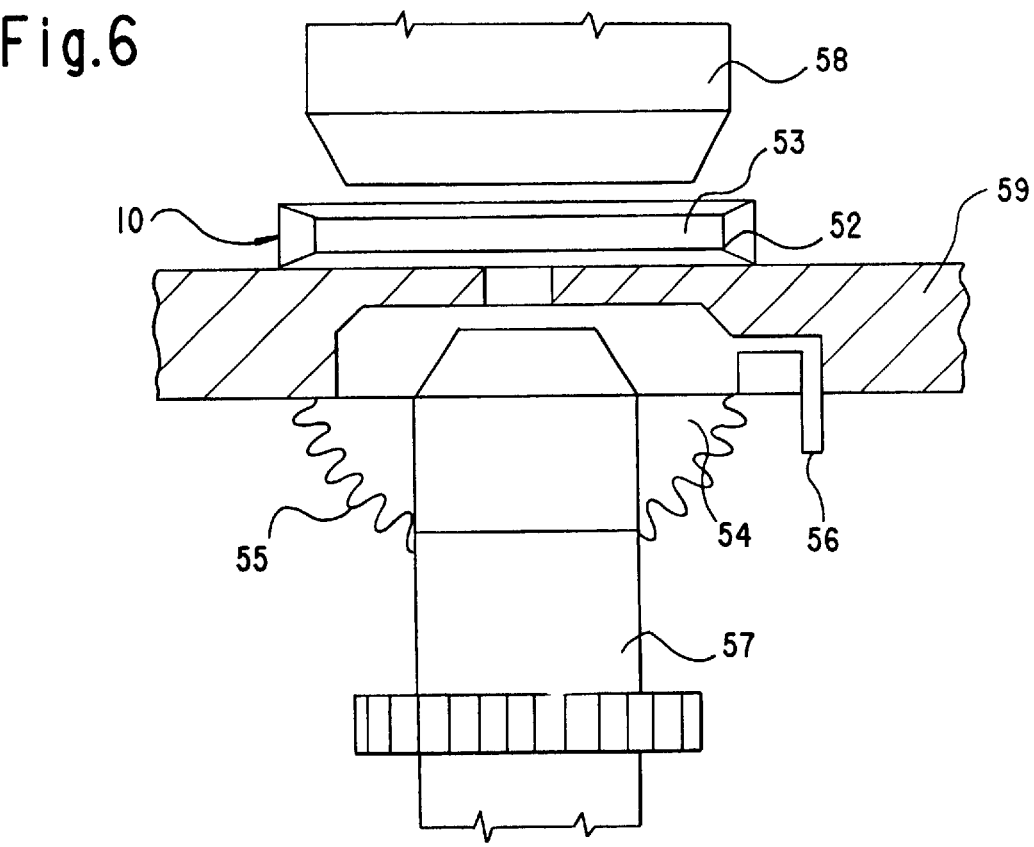

After having performed the sedimentation in centrifuge 40, cuvette 10 is slipped along the conveyor belt 17 over the optical unit 50. This position is shown in FIG. 6. The optical microscope unit 50 comprises an object platform, an objective 57 of the microscope located below it, and an illuminating device above it, the condenser 58 of which is shown in FIG. 6 (and 7). An opening 51 is provided in the object platform 59 in the center line of objective 59 and condenser 58. Cuvette 10 is arranged above the opening. Around opening the object platform 59 is thinned away, and this portion is covered with a vacuum-tight sealing 55. Sealing 55 is made of a resilient material permitting displacement of the objective 57 in axial direction. The space between sealing 55 and object platform 59 constituting a vacuum chamber 54 is linked up through vacuum tube 56 with a vacuum pump not shown in the figure. The upper surface of object platform 59 is bright-polished permitting the cuvette 10 to slide easily over it without scratching. In order to reduce friction, the object platform 59 can be provided with a friction-reducing layer.

When cuvette 10 is pushed over the opening, the vacuum chamber 54 is shut off by the cuvette, and the sucking effect of vacuum thus developing causes adherence of the baseplate 42 of cuvette 10 to the surface of object platform 59. The applied vacuum need not be high, since it only serves to hold cuvette 10 slightly in position and to remove the air layer from between the cuvette 10 and object platform 59. This weak vacuum also permits adjustment of the position of cuvette 10 over the opening. To render this corrective displacement of the cuvette possible, the vacuum applied may be reduced, but generally this is not necessary.

Thus, optical examination can be carried out with the sediment remaining in cuvette 10, since the fluid 53 above it will not impede optical examination. As a favourable characteristic of the arrangement complying with the invention, the baseplate 12 of cuvette 10 can be made of the same material as that of the coverplate used in conventional microscopic examinations, and the thickness of the baseplate can be e.g. 0.17 mm. The boundary planes of such a covering plate are parallel, and the thickness thereof can accurately be adhered to. Owing to that, assuming an objective with a magnifying power lying in the usual range of 10 to 40 and with apertures ranging from 0.5 to 0.8 usually of 0.65 and having a depth of focus between 1 to 3 μm, the optical examinations can be carried out without modifying the position of objective 57 of the microscope. Namely, in that case, the object of examinations is the sediment depositing on the baseplate 12 of cuvette 10, only the baseplate 12 being interposed between object and optical device, and optical conditions are not influenced by the fluid 53 floating above sediment 52 and by the coverplate 11 of cuvette 10. The spacing between cuvette 10 and microscope objective 57 is ensured with sufficient accuracy by the pressing force of vacuum acting on the cuvette 10. In order to make this spacing as accurate as possible, it is of special importance to select a resilient material for the baseplate 12 of cuvette 10 to ensure that it will exactly adapt itself to the surface of the object holder 59. Positioning within an accuracy of a few microns will thereby be possible, so that generally no readjustment of the focus from sample to sample will be required, which would be cumbersome and would require additional time consuming corrections.

Figure 7:
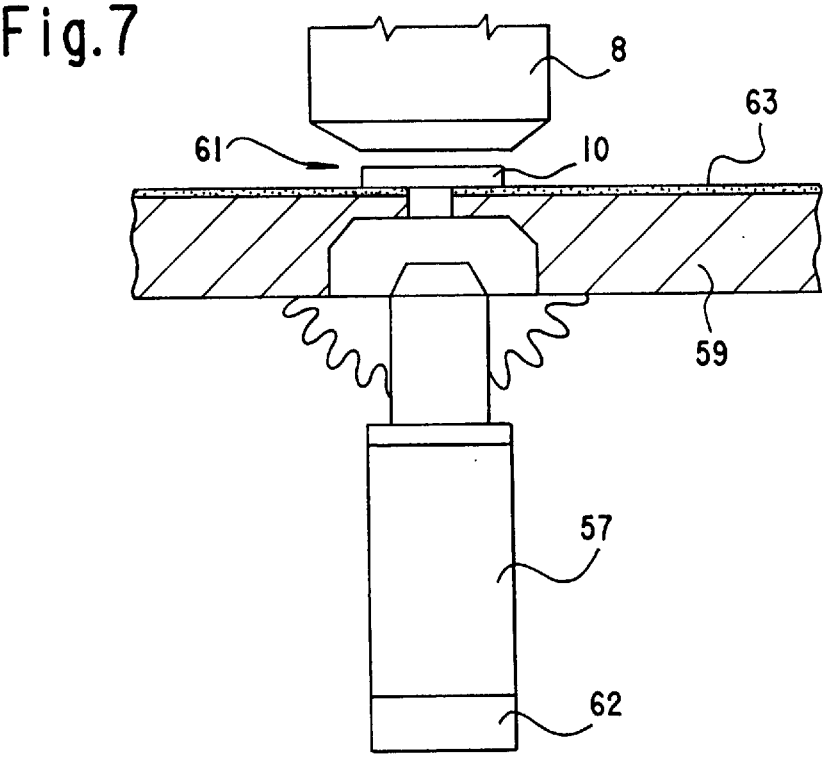

For automatic evaluation of samples contained in the cuvettes 10 the images appearing in the field of view of the microscope have to be digitalized in succession. In order to avoid errors resulting from uneven sedimentation, cuvette 10 can be placed in several different positions above opening, performing repeated optical examinations. In FIG. 7 an optical unit 60 equipped with a microscanner is shown, where to the microscope objective 57 a row of sensors 62 is coupled, by which a linear image is transformed into electric signals. For evaluation, cuvette 10 is displaced in the direction of feed 61 shown in the figure, the required information of the image resolved into lines is continuously available as output of the row of sensors. So, the image is scanned along each line, and this scanning repeated several times permits the optical evaluation of a coherent image of a size required. This arrangement is suitable for substituting a video-camera, providing means for a better digitalization of optical information obtained from the scanned image frame.

In the course of moving the cuvettes 10, continuous care should be taken to prevent stirring-up of the sediment 52. E.g. possible minor vibrations caused by sticking friction should be avoided by applying a friction reducing coating 63 to the object platform 59. Preferable material of this coating is PTF (polytetrafluor-ethylene).

The invented method and apparatus can be advantageously used for controlling waste water treatment, environment control, testing various suspensions in the course of their industrial production, cytological testing of body fluids both in human and veterinary medical examinations, other biochemical test in food and pharmaceutical industry.

I claim:

1. An apparatus suitable for centrifuging a sample liquid containing particles, the apparatus comprising
   a cuvette holder configured to receive a cuvette containing a sample liquid containing particles; and
   a centrifuge having a horizontal shaft which provides the axixs of rotation of the centrifuge and which is coupled to the cuvette holder such that the cuvette holder can assume a plurality of rotational positions about the horizontal shaft, and configured such that the cuvette holder is substantially horizontal when the cuvette holder is in a lowermost position relative to the horizontal shaft.

2. The apparatus of claim 1, further comprising
   optical means for optically examining the particles in the sample liquid; and
   conveying means for conveying the cuvette from the lowermost position of the cuvette holder to the optical means.

3. The apparatus of claim 2, further comprising dosing means for filling the cuvette with the sample liquid.

4. The apparatus of claim 1, further comprising a cuvette containing a sample liquid containing particles, wherein the cuvette is located in the cuvette holder and when the cuvette holder is in the lowermost position relative to the horizontal shaft, the cuvette is substantially horizontal.

5. The apparatus of claim 2, further comprising a cuvette containing a sample liquid containing particles, wherein the cuvette is located in the cuvette holder and when the cuvette holder is in the lowermost position relative to the horizontal shaft, the cuvette is substantially horizontal.

6. The apparatus of claim 4, wherein the cuvette has a planar shape.

7. The apparatus of claim 5, wherein the cuvette has a planar shape.

8. The apparatus of claim 1, wherein the horizontal shaft is coupled to the cuvette holder via a joint.

9. The apparatus of claim 8, wherein the joint is a fixed joint.

10. The apparatus of claim 8, wherein the joint has one degree of freedom.

11. The apparatus of claim 10, wherein the joint permits the cuvette holder to rotate around an axis parallel to the horizontal shaft.

12. The apparatus of claim 2, wherein the optical means comprises examining means for examining the particles in the sample liquid, and a horizontally-positioned object platform having an opening therein, wherein the examining means is located below the object platform and configured to optically examine the particles in the sample liquid through the opening when the cuvette is located over the opening.

13. The apparatus of claim 5, wherein
   the optical means comprises examining means for examining the particles in the sample liquid, and a horizontally-positioned object platform having an opening therein, wherein the examining means is located below the object platform and configured to optically examine the particles in the sample liquid through the opening when the cuvette is located over the opening, the examining means can, and
   the conveying means for conveying the cuvette from the lowermost position of the cuvette holder to the optical means is configured to convey the cuvette in a substantially horizontal orientation.

14. The apparatus of claim 12, wherein the examining means is coupled to the object platform by attaching means for attaching the examining means to the object platform, wherein the examining means, the object platform and the attaching means together define a vacuum chamber between the examining means and the object platform, and the vacuum chamber is configured to provide suction which presses the cuvette against the object platform when the cuvette is located over the opening.

15. The apparatus of claim 13, wherein the examining means is coupled to the object platform by attaching means for attaching the examining means to the object platform, wherein the examining means, the object platform and the attaching means together define a vacuum chamber between the examining means and the object platform, and the vacuum chamber is configured to provide suction which presses the cuvette against the object platform when the cuvette is located over the opening.

16. The apparatus of claim 3, further comprising conveying means for conveying the cuvette from the dosing means to the lowermost position of the cuvette holder.

17. A method of centrifuging a sample liquid containing particles, the method comprising introducing a cuvette containing a sample liquid containing particles into a cuvette holder which is coupled to a centrifuge having a horizontal shaft which provides the axis of rotation of the centrifuge, wherein the cuvette holder can assume a plurality of rotational positions about the horizontal shaft, and when the cuvette holder is in a lowermost position relative to the horizontal shaft, the cuvette holder is substantially horizontal; and centrifuging the sample liquid using the centrifuge.

18. The method of claim 17, further comprising, after said centrifuging step, conveying the cuvette from the lowermost position of the cuvette holder to an examining position; and optically examining the particles in the sample liquid in the examining position.

19. The method of claim 18, further comprising, before said introducing step, filling the cuvette with the sample liquid at a filling position and conveying the cuvette from the filling position to the lowermost position of the cuvette holder.

20. The method of claim 17, wherein when the cuvette holder having the cuvette introduced therein is in the lowermost position relative to the horizontal shaft, the cuvette is substantially horizontal.

21. The method of claim 18, wherein when the cuvette holder having the cuvette introduced therein is in the lowermost position relative to the horizontal shaft, the cuvette is substantially horizontal.

22. The method of claim 18, wherein, in said optically examining step, the particles are optically examined using examining means for examining the particles in the sample liquid and a horizontally-positioned object platform having an opening therein, wherein the examining means is located below the object platform, the cuvette is located over the opening, and the particles are optically examined through the opening.

23. The method of claim 21, wherein in said conveying step, the cuvette is conveyed from the lowermost position of the cuvette holder to the examining position in a substantially horizontal orientation, and in said optically examining step, the particles are optically examined using examining means for examining the particles in the sample liquid and a horizontally-positioned object platform having an opening therein, wherein the examining means is located below the object platform, the cuvette is located over the opening, and the particles are optically examined through the opening.

24. The method of claim 22, wherein the examining means is coupled to the object platform by attaching means for attaching the examining means to the object platform, wherein the examining means, the object platform and the attaching means together define a vacuum chamber between the examining means and the object platform, and the vacuum chamber provides suction which presses the cuvette against the object platform.

25. The method of claim 23, wherein the examining means is coupled to the object platform by attaching means for attaching the examining means to the object platform, wherein the examining means, the object platform and the attaching means together define a vacuum chamber between the examining means and the object platform, and the vacuum chamber provides suction which presses the cuvette against the object platform.

26. The method of claim 17, wherein, in said centrifuging step, the cuvette holder rotates around an axis parallel to the horizontal shaft.

27. The method of claim 17, wherein, in said centrifuging step, an acceleration ratio between a first acceleration component which acts perpendicular to the cuvette and a second acceleration component which acts parallel to the cuvette is at a value higher than 10.

28. The method of claim 17, wherein before and after said centrifugation step, the cuvette holder is in a same angular position relative to the horizontal shaft.

29. An apparatus suitable for centrifuging a sample liquid containing particles, the apparatus comprising a cuvette suitable for containing a sample liquid containing particles;

a cuvette holder configured to receive the cuvette; and a centrifuge having a horizontal shaft which provides the axis of rotation of the centrifuge and which is coupled to the cuvette holder such that the cuvette holder can assume a plurality of rotational positions about the horizontal shaft, and configured such that the cuvette holder and the cuvette are substantially horizontal when the cuvette is received in the cuvette holder and the cuvette holder is in a lowermost position relative to the horizontal shaft.

* * * * *